(12) United States Patent
Zvuloni

(10) Patent No.: US 7,604,605 B2
(45) Date of Patent: Oct. 20, 2009

(54) DEVICE, SYSTEM, AND METHOD FOR DETECTING AND LOCALIZING OBSTRUCTION WITHIN A BLOOD VESSEL

(75) Inventor: Roni Zvuloni, Haifa (IL)

(73) Assignee: Galil Medical Ltd., Yokneam (IL)

( * ) Notice: Subject to any disclaimer, the term of this patent is extended or adjusted under 35 U.S.C. 154(b) by 0 days.

(21) Appl. No.: 10/542,386

(22) PCT Filed: Jan. 15, 2004

(86) PCT No.: PCT/IL2004/000043

§ 371 (c)(1),
(2), (4) Date: Nov. 30, 2005

(87) PCT Pub. No.: WO2004/062525

PCT Pub. Date: Jul. 29, 2004

(65) Prior Publication Data

US 2006/0149166 A1    Jul. 6, 2006

Related U.S. Application Data

(60) Provisional application No. 60/440,361, filed on Jan. 16, 2003.

(51) Int. Cl.
*A61B 5/103* (2006.01)
*A61B 5/02* (2006.01)

(52) U.S. Cl. .................. 600/587; 600/488; 600/486; 600/424; 600/481

(58) Field of Classification Search ............. 600/424; 606/108, 12
See application file for complete search history.

(56) References Cited

U.S. PATENT DOCUMENTS

| | | | |
|---|---|---|---|
| 3,831,588 A | 8/1974 | Rindner | |
| 4,211,233 A | 7/1980 | Lin | |
| 4,301,677 A * | 11/1981 | Fisher | 73/105 |
| 4,873,990 A * | 10/1989 | Holmes et al. | 600/561 |
| 4,901,731 A * | 2/1990 | Millar | 600/488 |
| 5,178,153 A | 1/1993 | Einzig | |
| 5,259,837 A | 11/1993 | Van Wormer | |
| 5,752,522 A | 5/1998 | Murphy | |

(Continued)

FOREIGN PATENT DOCUMENTS

WO    WO 96/07351    3/1996

(Continued)

OTHER PUBLICATIONS

International Search Report Dated Nov. 16, 2004 From the International Searching Authority Re.: Application No. PCT/IL04/00046.

(Continued)

*Primary Examiner*—Eric F Winakur
*Assistant Examiner*—Helene Bor

(57) ABSTRACT

The present invention is of system, device, and method for detecting and localizing obstruction in a blood vessel. More particularly, the present invention is of a balloon catheter having an expandable balloon which comprises a plurality of strain gauges operable to report relative degrees of expansion of local portions of a wall of the expandable balloon. Incomplete expansion of a local portion of the balloon, under common pressure within the balloon, indicates presence of an obstruction, such as a region of plaque, within the blood vessel.

38 Claims, 2 Drawing Sheets

U.S. PATENT DOCUMENTS

| | | | |
|---|---|---|---|
| 5,860,923 A | | 1/1999 | Lenker et al. |
| 5,865,801 A | | 2/1999 | Houser |
| 5,871,449 A | * | 2/1999 | Brown .................. 600/474 |
| 5,902,308 A | * | 5/1999 | Murphy ................ 606/108 |
| 5,924,984 A | | 7/1999 | Rao |
| 6,053,873 A | * | 4/2000 | Govari et al. ............ 600/505 |
| 6,081,737 A | * | 6/2000 | Shah .................... 600/393 |
| 6,427,089 B1 | | 7/2002 | Knowlton |
| 6,602,246 B1 | | 8/2003 | Joye et al. |
| 6,615,071 B1 | * | 9/2003 | Casscells et al. ........ 600/474 |
| 7,081,096 B2 | * | 7/2006 | Brister et al. ........... 600/549 |
| 7,181,261 B2 | * | 2/2007 | Silver et al. ............ 600/345 |
| 2002/0055674 A1 | * | 5/2002 | Ben-Haim et al. ....... 600/374 |
| 2002/0115931 A1 | | 8/2002 | Strauss et al. |
| 2003/0105388 A1 | * | 6/2003 | Roy et al. ............... 600/300 |
| 2004/0138548 A1 | * | 7/2004 | Strommer et al. ........ 600/407 |
| 2004/0230131 A1 | * | 11/2004 | Kassab et al. ........... 600/547 |
| 2005/0049475 A1 | * | 3/2005 | Gregersen .............. 600/407 |
| 2005/0203434 A1 | * | 9/2005 | Kassab .................. 600/547 |
| 2006/0004286 A1 | * | 1/2006 | Chang et al. ............ 600/435 |
| 2006/0122522 A1 | * | 6/2006 | Chavan et al. ........... 600/505 |
| 2006/0254600 A1 | * | 11/2006 | Danek et al. ............ 128/898 |
| 2007/0066929 A1 | * | 3/2007 | Ferren et al. ............ 604/8 |

FOREIGN PATENT DOCUMENTS

| | | |
|---|---|---|
| WO | WO 00/35342 | 6/2000 |
| WO | WO 02/101347 | 12/2002 |
| WO | WO 2004/062526 | 7/2004 |

OTHER PUBLICATIONS

Supplementary European Search Report Dated Apr. 6, 2009 From the European Patent Office Re.: Application No. 04702402.1.

Supplementary European Search Report Dated Apr. 24, 2009 From the European Patent Office Re.: Application No. 04702399.9.

Written Opinion Dated Nov. 16, 2004 From the International Searching Authority Re.: Application No. PCT/IL04/00046.

De Korte et al. "IVUS Elastography: A Potential Identifier of Vulnerable Atherosclerotic Plaque", 1998 IEEE Ultrasonic Symposium Proceedings, XP002523215, 2: 1729-1732, Oct. 5, 1998.

* cited by examiner

DEVICE, SYSTEM, AND METHOD FOR DETECTING AND LOCALIZING OBSTRUCTION WITHIN A BLOOD VESSEL

RELATED PATENT APPLICATION

This application is a National Phase Application of PCT/IL2004/000043 having International Filing Date of 15 Jan. 2004, which claims the benefit of U.S. Provisional Patent Application No. 60/440,361 filed 16 Jan. 2003. The contents of the above Application are all incorporated herein by reference.

FIELD AND BACKGROUND OF THE INVENTION

The present invention relates to devices and methods for detection and diagnostic localization of plaque-induced stenosis in a blood vessel. More particularly, the present invention relates to an expandable balloon catheter insertable into a blood vessel, which catheter comprises a plurality of strain gauges operable to report differential expansion of portions the balloon catheter under common pressure, thereby indicating the position and extent of regions of plaque within the vessel The device optionally includes radio-opaque markers to facilitate diagnostic interpretation of the strain-gauge output.

Most adults suffer to some degree from artherosclerotic plaque within blood vessels of the body. Plaque may limit blood flow through the vessel, causing dangerous tissue degeneration in extreme cases. Stenosis caused by plaque is often responsible for ischemic heart disease. The presence of plaque in blood vessels may also lead to thrombosis, endangering heart, lung, and brain tissue in particular.

Percutaneous transluminal angioplasty (PTA) is a treatment of choice for most stenotic conditions. In PTA, an inflatable balloon catheter or similar device is used to dilate a stenotic region of a blood vessel, thereby facilitating blood flow through the affected region. Various alternative and/or complementary procedures are used in treatment of stenotic conditions. These include arthrectomy, laser angioplasty, the use of stents, and the use of cryosurgical techniques to cool affected regions during or following compression of an affected area by angioplasty balloon.

The effectiveness of the above treatment methodologies is highly dependent on correct diagnostic localization of the areas to be treated. Yet, stenotic areas are, by their nature, not easily observable. A variety of strategies for locating regions of plaque within a blood vessel, and for characterizing that plaque, have been proposed and tested. Joye et al., in U.S. Pat. No. 6,602,246, teaches methods based on differential temperature readings from within a blood vessel, in recognition of the fact that the type of plaque particularly prone to create thromboses, termed "vulnerable plaque", tends to be inflamed and therefore is at a higher temperature than standard stenotic plaque and normal healthy vascular tissue. Joye also lists angiography, intravascular ultrasound, angioscopy, magnetic resonance imaging, magnetic resonance diffusion imaging; spectroscopy, infrared spectroscopy, scintigraphy, optical coherence tomography, electron beam computed tomographic scanning, and thermography as prior art methods which have been used, with varying success, to locate regions of plaque within a vessel.

None of the above methods, however, has been found to be entirely successful, and most are complex and expensive. Thus there is a widely felt need for, and it would be advantageous to have, a device and method for locating and characterizing stenotic regions within a blood vessel, which device and method are relatively simple in construction and use, and relatively inexpensive.

SUMMARY OF THE INVENTION

According to one aspect of the present invention there is provided a balloon catheter operable to detect and report obstructions in a blood vessel, comprising an expandable balloon and a plurality of strain gauges each operable to report a degree of expansion of a local portion of a wall of the expandable balloon.

The strain gauges may be mounted on the balloon's wall outside of the balloon or inside the balloon, or may be embedded in a wall of the balloon.

Preferably, a plurality of the strain gauges is mounted in a circumferential configuration around the balloon. Further preferably, the strain gauges may be mounted in a plurality of circumferential configurations.

Preferably, the catheter further comprising a radio-opaque marker or a plurality of radio-opaque markers mounted in an asymmetric configuration.

The catheter may also comprise an ultrasound marker distinguishable under ultrasound imaging, or a plurality of ultrasound markers distinguishable under ultrasound imaging, mounted in an asymmetric configuration.

The strain gauges may be operable to report strain through a wire connection or through a wireless connection.

According to another aspect of the present invention there is provided a method for detecting obstruction in a blood vessel, comprising:

a. introducing into the blood vessel a balloon catheter having an expandable balloon which comprises a plurality of strain gauges operable to measure and report degrees of expansion of local portions of a wall of the expandable balloon;

b. expanding the balloon within the blood vessel;

c. comparing expansions reported by a plurality of strain gauges; and d. reporting obstruction of the blood vessel if at least one of the plurality of strain gauges reports less expansion than another of the strain gauges.

The method may further comprise determining a position of the balloon in a body of a patient when the balloon is positioned within the artery at a position at which obstruction of the blood vessel is so reported. Determining the position of the balloon may be accomplished by observing, using an x-ray visualization modality, a radio-opaque marker of the balloon, or, preferably, by observing a plurality of radio-opaque markers. Alternatively, position of the balloon may be determined by observing, using an ultrasound visualization modality, an ultrasound-distinguishable marker disposed at a known position on or in the balloon.

The method preferably further comprises displaying, in a graphics display, an image of a portion of a body of a patient, obtained through use of a medical imaging modality, integrated with an image of detected plaque within the blood vessel.

According to yet another aspect of the present invention there is provided a system for detecting and localizing obstructing material in a blood vessel, comprising:

a. an expandable balloon catheter having an expandable balloon which comprises a plurality of strain gauges operable to measure and report local expansion of portions of the expandable balloon b. a data analysis module operable to calculate an analysis of data received from the plurality of strain gauges.

Preferably, the data analysis module is further operable to record, in a memory module, data reported by the strain gauges. The system may further comprise such a memory module.

Preferably, the data analysis module comprises a graphics display.

Preferably, the data analysis module is operable to calculate a first image of a blood vessel showing regions of obstruction therein, as indicated by data obtained from the strain gauges.

Preferably, the data analysis module is further operable to integrate the first image of the blood vessel with a second image produced by a standard imaging modality, such as a fluoroscopic image or an ultrasound image.

According to further features in preferred embodiments of the invention described below, the system is operable to display, on a graphics display, an image obtained from a medical imaging modality such as a fluoroscope or an ultrasound system.

Preferably, the data analysis module is operable to modify this image so as to represent, on the modified image, areas of obstruction of a blood vessel as determined by the analysis of the data from the plurality of strain gauges.

The strain gauges of the system may be mounted inside or outside the wall of the expandable balloon, or be embedded in that wall.

The strain gauges of the system are preferably mounted in a circumferential configuration around the balloon, or in a plurality of circumferential configurations.

Preferably, the balloon comprises one or more radio-opaque markers on the balloon.

Alternatively or additionally, the balloon may comprise one or more ultrasound marker distinguishable under ultrasound imaging, preferably mounted on the balloon in an asymmetric configuration.

The strain gauges of the system may be operable to report strain to the data analysis module through a wire connection, or through a wireless connection.

The present invention successfully addresses the shortcomings of the presently known configurations by providing a device and method for locating and characterizing stenotic regions within a blood vessel, which device and method are relatively simple to construct and to use, and relatively inexpensive.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A shows the balloon in an unexpanded state, FIG. 1B shows the balloon in an expanded state.

DESCRIPTION OF THE PREFERRED EMBODIMENTS

Figure 1A:
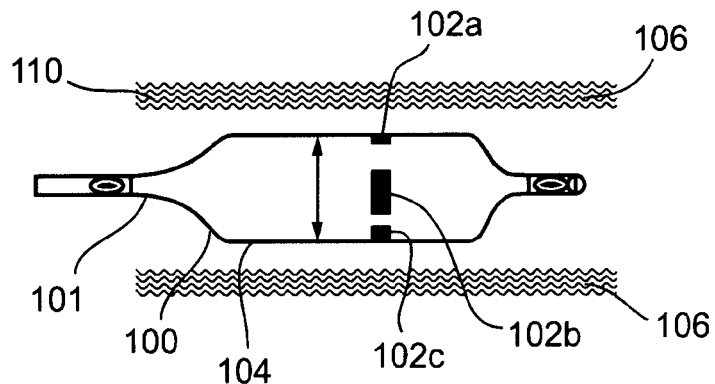
FIGS. 1A and 1B present simplified schematics of a balloon catheter having an expandable balloon comprising a plurality of strain gauges distributed along a circumference of the balloon.

The present invention relates to devices and methods for detection and localization of plaque within a blood vessel. More particularly, the present invention relates to an expandable balloon catheter insertable into a blood vessel, which catheter comprises a plurality of strain gauges operable to report differential expansion of portions the balloon catheter under common pressure, thereby indicating the position and extent of regions of plaque within the vessel. The device optionally includes radio-opaque markers to facilitate diagnostic interpretation of the strain-gauge output.

The principles and operation of a diagnostic balloon catheter specialized for detecting and localizing plaque within a blood vessel according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Attention is now drawn to FIG. 1, which presents a simplified schematic of a balloon catheter 101 which comprises an expandable balloon 100 and a plurality of strain gauges 102a, 102b, 102c etc. distributed along a circumference of balloon 100. Strain gauges 102 are preferably distributed along the external surface of balloon 100, or alternately are embedded in wall 104 of balloon 100, or mounted along an internal surface of balloon 100.

Figure 1B:
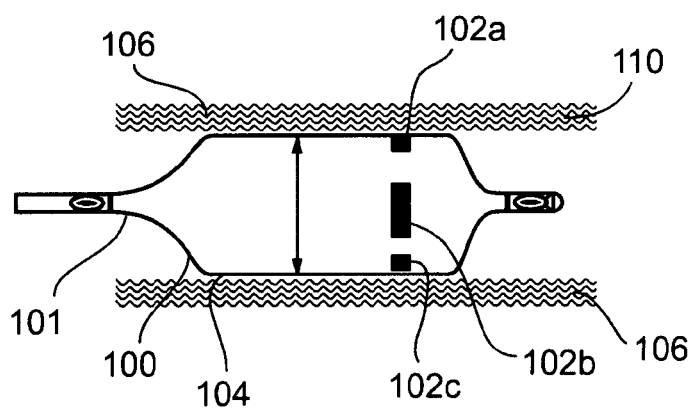

Expansion of balloon 100 is shown in a transition from FIG. 1A, where an unexpanded balloon 100 is not everywhere adjacent to blood vessel wall 106 of blood vessel 110, to a situation depicted in FIG. 1B where balloon 100 has been expanded to fill vessel blood vessel 110, causing the circumference of balloon 100 to be everywhere adjacent to vessel wall 106 of vessel 110. Expansion of balloon 100 as shown in FIG. 1B is accompanied by expansion of strain gauges 102 embedded in or attached to wall 104 of balloon 100.

Each strain gauge 102 is operable to measure and to report local tangential strains in balloon wall 104 in its vicinity. Strain gauges 102 may be designed and constructed to report through by means of a wire connection, e.g., by modifying an electrical resistance value as a function of detected strain in the gauge. Alternatively, strain gauges 102 may be designed and constructed to report strain values through a wireless communication module.

Figure 2A:
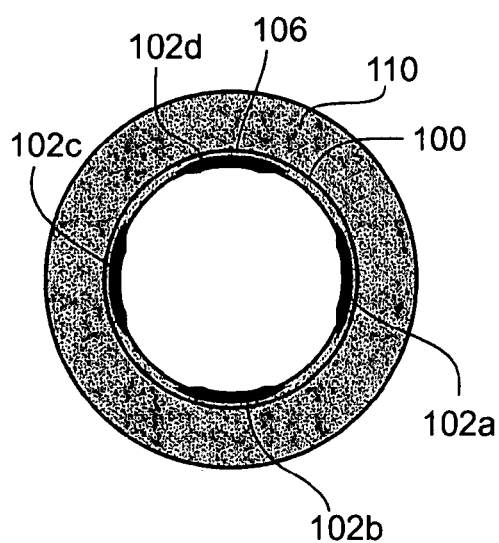
FIGS. 2A and 2B are simplified schematics of a cross-section of the balloon of FIG. 1, showing how differential readings of the strain gauges can be used to detect and measure obstructing material, such as plaque, within a blood vessel.
Figure 2B:
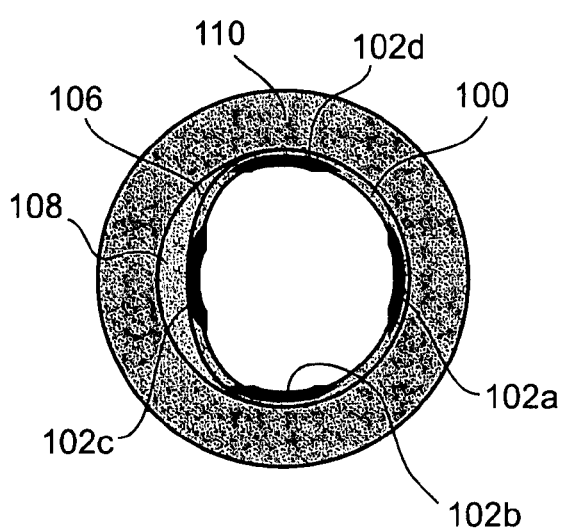

Attention is now drawn to FIG. 2, which is a simplified schematic of a cross-section of balloon 100, showing a plurality of strain gauges 102 arranged around a circumference of balloon 100. FIGS. 2A and 2B shown how balloon 100, comprising strain gauges 102, can be used to detect and measure obstructing material, such as plaque, within the walls 106 of blood vessel 110.

FIG. 2A shows balloon 100 fully expanded within the confines of vessel wall 106 of blood vessel 100. In the situation depicted in FIG. 2A, no obstruction is present in vessel 110. Consequently, the degree of expansion experienced by strain gauges 102a, 102b, 102c, and 102d is substantially equal. Thus, report of substantially equal strains measured by strain gauges 102a, 102b, 102c, and 102d constitutes a diagnostic indication that vessel 110, at the location shown in the cross-section presented in FIG. 2A, is substantially free of obstruction, free of plaque.

Attention is now drawn to FIG. 2B, presenting a cross-section of a segment of blood vessel 110 wherein an obstructing material, such as a region of plaque here designated 108, is present within vessel wall 106. As balloon 100 expands and touches portions of the inner vessel wall 106, friction of the contact between balloon wall 104 and vessel wall 108 substantially prevents tangential slipping of balloon wall 104. Balloon 100 is preferably constructed of a highly flexible elastomer with little tendency to slip sideways when in contact with a vessel wall (this is a characteristic of most of elastomers).

In the situation presented in FIG. 2B, the presence of plaque region 108 partially prevents full expansion of that portion of balloon wall 104 which is contiguous to strain gauge 102c. Consequently, as shown in FIG. 2B, strain gauge 102c will report a lesser degree of expansion than that reported by strain gauges 102a, 102b, and 102d. Such differential expansion, measured and reported by strain gauges 102, constitutes a diagnostic sign that the portion of vessel wall 104 which is contiguous to strain gauge 102c presents an obstructing material such as plaque. Differences in the expansion reported by the various strain gauges 102a-102d permits to calculate position and degree of obstruction around the circumference of balloon 100.

Figure 3:
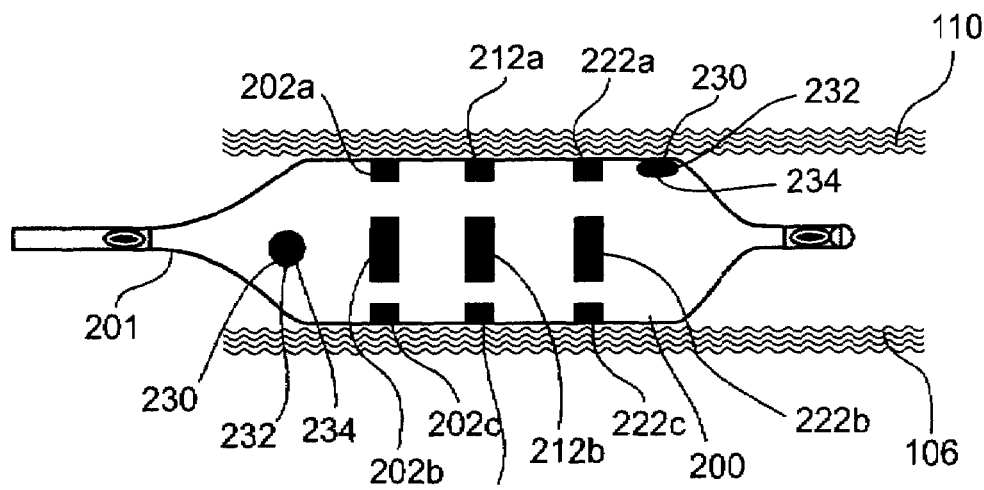
FIG. 3 presents a simplified schematic of a balloon catheter which comprises several sets of strain gauges, arranged both circumferentially and longitudinally, along and around an expandable balloon.

Attention is now drawn to FIG. 3, which presents a simplified schematic of a balloon catheter 201 which comprises an expandable balloon 200. Balloon 200 comprises a plurality of strain gauges arranged both circumferentially and longitudinally, along and around balloon 200. As may be seen from FIG. 3, strain gauges 202a, 202b, and 202c and 202d (not shown) present the configuration discussed above with respect to FIGS. 1 and 2. Strain gauges 212a, 212b, 212c and 212d (not shown) present a similar configuration, at a more distal portion of balloon 200, and strain gauges 222a, 222b, 222c, and 222d (not shown) present a similar configuration at a yet more distal portion of balloon 200. Thus, the configuration presented by FIG. 3 enables simultaneous measurement of constrictions in vessel 110 at a plurality of longitudinal positions, which measurements present, in each case, information as to the size and position of a plaque deposit or other obstructing feature within vessel 110 at that longitudinal position. Balloon 200 can, of course, be decompressed and advanced or retracted within vessel 110, then again expanded to effect a new set of measurements at a new position, until all portions of vessel 110 of interest to a diagnostician operating balloon 200 have been measured.

FIG. 3 presents an additional feature of balloon 200, useful for clinical diagnosis: balloon 200 optionally comprises one or more marker elements 230, such as radio-opaque elements 232. Radio-opaque elements 232 are easily visible in a fluoroscope or an x-ray photograph. Consequently, a fluoroscopic or x-ray photograph shows clearly the position of balloon 200 with respect to various anatomical markers. If balloon 200 is photographed in a selected position, and strain gauge measurements are taken and recorded while balloon 200 is at the photographed position, then the position of plaque deposits so detected may easily be related to the position of various other anatomical features and structures, thereby facilitating therapeutic treatment of the detected obstruction. Similarly, markers 230 may be ultrasound-visible elements 234, useable to make the position of balloon 200 visible and photographable under ultrasound imaging. Also similarly, graduated length markings on a proximal portion of balloon catheter 101, operable to report a distance of penetration of balloon 200 into vessel 110, may be similarly used to record a position of balloon 200 when obstruction has been detected.

Figure 4:
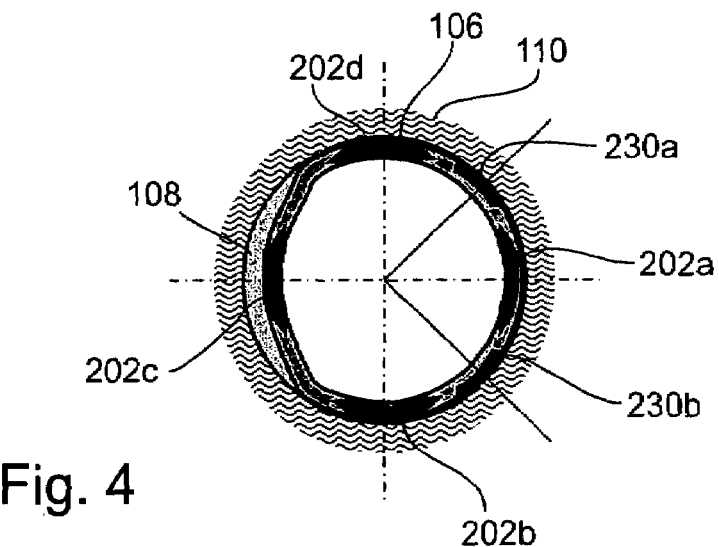
FIG. 4 presents a simplified cross-sectional view of the balloon of FIG. 3.

Radio-opaque markers 232 or ultrasound-visible elements 234 are preferably disposed asymmetrically, so as to render visible, under appropriate visualization modalities, orientation of balloon 200 as well as depth of penetration of balloon 200 in vessel 110. FIG. 4, which presents a cross-sectional view of balloon 200, shows asymmetric positioning (grouped around strain gauge 202a) of markers 230a and 230b.

Figure 5:
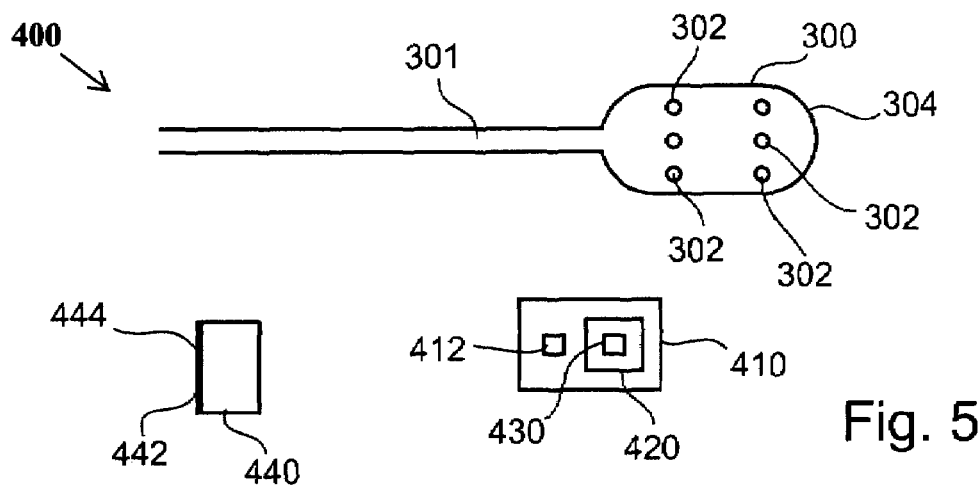
FIG. 5 presents a system for detecting and localizing obstructions in a blood vessel.

Attention is now drawn to FIG. 5, which presents a system 400 for detecting and localizing obstructions in a vessel. System 400 comprises a balloon catheter 301 comprising. an expandable balloon 300 which may be constructed according to the descriptions of balloon catheters 101 and 201 described above. System 400 further comprises a data analysis module 410 operable to receive reports from a plurality of strain gauges 302 disposed at various positions on or in wall 304 of balloon 300. Preferably, data analysis module 410 is further operable to combine data reports from a plurality of strain gauges 302, to calculate an integrated analysis of data so received, to record both data and analysis in a memory module 412 such as a hard disk, and to present an integrated graphics image 430 of the analyzed result on a graphics display 420. Integrated graphics image 430 preferably combines, in a common display, both analysis of data from strain gauges 302, and graphics data generated by a visualization modality 440 such as a fluoroscope 442 or an ultrasound system 444.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A balloon catheter operable to detect and report obstructions in a blood vessel, comprising:
   a. an expandable balloon; and
   b. a plurality of sets of strain gauges, each set comprising a plurality of gauges mounted on a circumference of said balloon at a common longitudinal distance alone said balloon, and each of said strain gauges being operable to report a degree of expansion of a local portion of a wall of said balloon in a vicinity of said each strain.

2. The catheter of claim 1, wherein at least one of said strain gauges is mounted external to a wall of said balloon.

3. The catheter of claim 1, wherein at least one of said strain Gauges is mounted internal to a wall of said balloon.

4. The catheter of claim 1, wherein at least one of said strain Gauges is embedded in a wall of said balloon.

5. The catheter of claim 1, further comprising a radio-opaque marker.

6. The catheter of claim 5, comprising a plurality of radio-opaque markers mounted in an asymmetric configuration.

7. The catheter of claim 1, further comprising an ultrasound marker distinguishable under ultrasound imaging.

8. The catheter of claim 7, comprising a plurality of ultrasound markers distinguishable under ultrasound imaging, mounted in an asymmetric configuration.

9. The catheter of claim 1, wherein said strain gauges are operable to report strain through a wire connection.

10. The catheter of claim 1, wherein said strain gauges are operable to report strain through a wireless connection.

11. A method for detecting obstruction in a blood vessel, comprising:
   a. introducing into said blood vessel a balloon catheter having an expandable balloon which comprising a plurality of strain gauges mounted on a circumference of said balloon at a common longitudinal distance along said balloon and operable to measure and report degrees of expansion of local portions of a wall of said balloon;
   b. expanding said balloon within said blood vessel;
   c. comparing expansions reported by said plurality of strain gauges; and
   d. reporting obstruction of said blood vessel if at least one strain gauge of said plurality of strain gauges report less expansion than another strain gauge of said plurality of strain gauges.

12. The method of claim 11, further comprising determining a position of said balloon in a body of a patient when said balloon is positioned within said artery at a position at which obstruction of said blood vessel is so reported.

13. The method of claim 12, further comprising determining said position of said balloon by observing, using an x-ray visualization modality, a radio-opaque marker of said balloon.

14. The method of claim 13, further comprising observing a plurality of radio-opaque markers.

15. The method of claim 12, wherein said position of said balloon is determined by observing, using an ultrasound visualization modality, an ultrasound-distinguishable marker disposed at a known position in said balloon.

16. The method of claim 12, further comprising displaying, in a graphics display, an image of a portion of a body of a patient, obtained through use of a medical imaging modality, integrated with an image of detected plaque within said blood vessel.

17. A system for detecting and localizing obstructing material in a blood vessel, comprising:
   a. an expandable balloon catheter having an expandable balloon which comprises a plurality of strain gauges operable to measure and report local expansion of portions of said expandable balloon, said plurality of strain gauges being mounted on a circumference of said balloon at a common longitudinal distance along said balloon; and
   b. a data analysis module which compares data received from said plurality of strain gauges and reports obstruction of said blood vessel if at least one strain gauge of said plurality of strain gauges reports less expansion than another strain gauge of said plurality of strain gauges.

18. The system of claim 17, wherein said data analysis module is operable to record in a memory module data reported by said strain gauges.

19. The system of claim 18, further comprising said memory module.

20. The system of claim 17, wherein said data analysis module comprises a graphics display.

21. The system of claim 17, wherein said data analysis module is operable to calculate a first image of a blood vessel showing regions of obstruction therein, as indicated by data obtained from said strain gauges.

22. The system of claim 21, wherein said data analysis module is further operable to integrate said first image of said blood vessel with a second image produced by a standard imaging modality.

23. The system of claim 22, wherein said second image is a fluoroscopic image.

24. The system of claim 22, wherein said second image is an ultrasound image.

25. The system of claim 17, further operable to display, on a graphics display, an image obtained from a medical imaging modality.

26. The system of claim 25, wherein said imaging modality is a fluoroscope.

27. The system of claim 25, wherein said imaging modality is an ultrasound system.

28. The system of claim 25, wherein said data analysis module is operable to modify said image so as to represent, on said modified image, areas of obstruction of a blood vessel as determined by said analysis of said data from said plurality of strain gauges.

29. The system of claim 17, wherein at least one of said strain gauges is mounted external to a wall of said balloon.

30. The system of claim 17, wherein at least one of said strain gauges is mounted internal to a wall of said balloon.

31. The system of claim 17, wherein at least one of said strain gauges is embedded in a wall of said balloon.

32. The system of claim 17, further comprising a plurality of sets of strain gauges, each set being arranged at a different axial position along said balloon.

33. The system of claim 17, further comprising a radio-opaque marker on said balloon.

34. The system of claim 33, comprising a plurality of radio-opaque markers mounted in an asymmetric configuration.

35. The system of claim 17, wherein said balloon comprises an ultrasound marker distinguishable under ultrasound imaging.

36. The system of claim 35, wherein said balloon comprises a plurality of ultrasound markers distinguishable under ultrasound imaging, mounted in an asymmetric configuration.

37. The system of claim 17, wherein said strain gauges are operable to report strain to said data analysis module through a wire connection.

38. The system of claim 17, wherein said strain gauges are operable to report strain to said data analysis module through a wireless connection.

* * * * *